US00PP26600P2

(12) United States Plant Patent
Hokanson et al.

(10) Patent No.: US PP26,600 P2
(45) Date of Patent: Apr. 12, 2016

(54) ***RHODODENDRON* PLANT NAMED 'UMNAZ 493'**

(50) Latin Name: *Rhododendron hybrida*
Varietal Denomination: UMNAZ 493

(71) Applicants: Stan C. Hokanson, St. Paul, MN (US); Steve McNamara, Victoria, MN (US)

(72) Inventors: Stan C. Hokanson, St. Paul, MN (US); Steve McNamara, Victoria, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 171 days.

(21) Appl. No.: 13/999,110

(22) Filed: Jan. 14, 2014

(51) Int. Cl.
*A01H 5/02* (2006.01)

(52) U.S. Cl.
USPC ..... Plt./239

(58) Field of Classification Search
USPC ..... Plt./239
See application file for complete search history.

(56) References Cited

PUBLICATIONS

Hokanson. *Rhododendrons* et compagnie vol. 4, No. 3, 2012, pp. 1-11.*

SDL Free Translation and Professional Translation Service, retrieved on Aug. 19, 2015, retrieved from the Internet at <www.freetranslation.com/en/translate-english-french> translation of p. 8 of Hokanson reference, 2 pp.*

* cited by examiner

*Primary Examiner* — June Hwu
(74) *Attorney, Agent, or Firm* — Penny J. Aguirre

(57) ABSTRACT

A new cultivar of hybrid *Rhododendron* plant named 'UMNAZ 493' that is characterized by its floriferous blooming habit and an extended bloom period that begins in late May to early June in Chanhassen, Minn. and lasts for up to 6 weeks, its abundance of fragrant, double flowers that are pink in color, its upright, mounded and densely branched plant habit reaching 2.2 m in height and 1.9 m in spread, and its good cold hardiness with flower buds that are resistant to cold damage and consistently bloom even when exposed to temperatures as low as −30° F.

2 Drawing Sheets

STATEMENT REGARDING FEDERALLY SPONSORED RESEARCH

This invention was made with government support under MN-22-055 awarded by the U.S. Dept. of Agriculture. The government has certain rights in the invention.

Botanical classification: *Rhododendron hybrida.*

Cultivar designation: 'UMNAZ 493'.

BACKGROUND OF THE INVENTION

The present invention relates to a new and distinct cultivar of *Rhododendron* plant of hybrid origin, botanically known as *Rhododendron hybrida* 'UMNAZ 493' and will be referred to hereafter by its cultivar name, 'UMNAZ 493'. 'UMNAZ 493' is a new cultivar of deciduous *Rhododendron* grown for use as a landscape plant.

The new cultivar was developed through an on-going breeding program conducted by the Inventors in Excelsior, Minn. The objectives of the breeding program are to develop new cultivars of *Rhododendron* that exhibit cold tolerance, excellent floral displays, disease-resistant foliage, and compact, deciduous plant habits. The new cultivar was derived from a cross made by the Inventors on May 23, 1988 between an unnamed proprietary plant in the Inventor's breeding program, *Rhododendron hybrida* UMN accession no. 19840940, as the female parent and an unnamed plant of *Rhododendron atlanticum* as the male parent. The Inventors selected 'UMNAZ 493' as a single unique plant amongst the seedlings that resulted from the above cross in June 1994.

Asexual propagation of the new cultivar was first accomplished by softwood stem cuttings in Excelsior, Minn. in June 1994—by one of the Inventors. Asexual propagation by softwood stem cuttings and tissue culture has determined that the characteristics of the new cultivar are stable and are reproduced true to type in successive generations.

SUMMARY OF THE INVENTION

The following traits have been repeatedly observed and represent the characteristics 'UMNAZ 493'. These attributes in combination distinguish 'UMNAZ 493' as a new and distinct cultivar of *Rhododendron.*

1. 'UMNAZ 493' exhibits a floriferous blooming habit and an extended bloom period that begins in late May to early June in Chanhassen, Minn. and lasts for up to 6 weeks.
2. 'UMNAZ 493' exhibits an upright, mounded and densely branched plant habit reaching 2.2 m in height and 1.9 m in spread.
3. 'UMNAZ 493' exhibits an abundance of fragrant, double flowers that are pink in color.
4. 'UMNAZ 493' exhibits good cold hardiness with flower buds that are resistant to cold damage and consistently bloom even when exposed to temperatures as low as −30° F.

The female parent of 'UMNAZ 493', 'UMN accession no. 19840940', differs from 'UMNAZ 493' in having less cold hardiness, in being less floriferous, and in being single flowered. The male parent, an unnamed plant of *Rhododendron*

*atlanticum*, differs from 'UMNAZ 493' in having less cold hardiness and flower bud resistance to cold, and in having single flowers that are smaller in size and pinkish white in color. 'UMNAZ 493' can also be most closely compared to the *Rhododendron* cultivars 'Chelsea Ranch' (not patented) and 'Cannon's Double' (not patented). Both are similar to 'UMNAZ 493' in being double flowered. 'Chelsea Ranch' differs from 'UMNAZ 493' in having flowers that are creamy white in color, and in having flower buds that are less cold tolerant. 'Cannon's Double' differs from 'UMNAZ 493' in having flowers that are creamy white in color with a pink blush, and in having flower buds that are less cold tolerant.

BRIEF DESCRIPTION OF THE DRAWINGS

The accompanying colored photographs were taken of a 24 year-old plant of the new cultivar as grown outdoors in an evaluation nursery in Excelsior, Minn.

The photograph in FIG. 1 provides a view of the overall plant habit of 'UMNAZ 493' in bloom.

Figure 1:
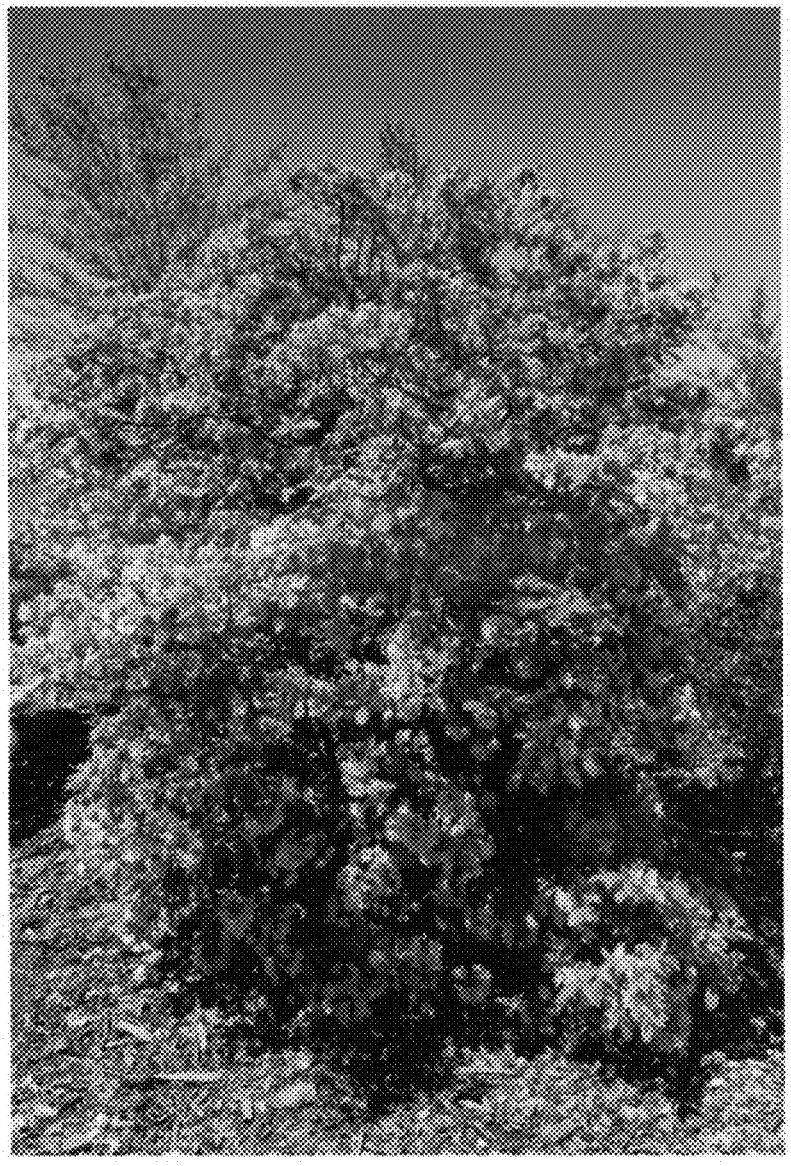
Figure 2:
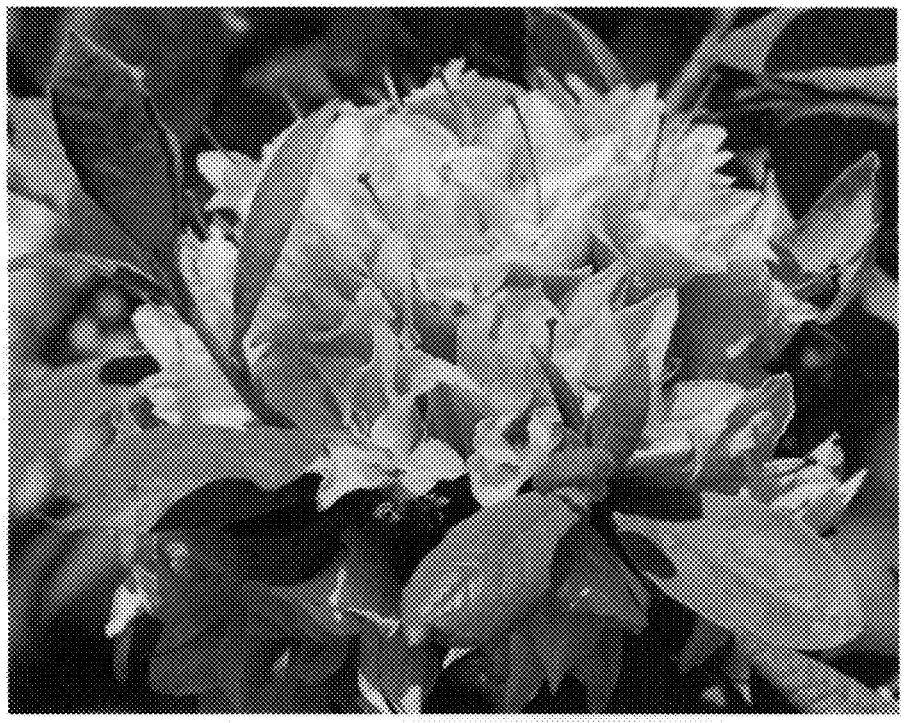

The photograph in FIG. 2 provides a close-up view of an inflorescence of 'UMNAZ 493'.

Figure 3:
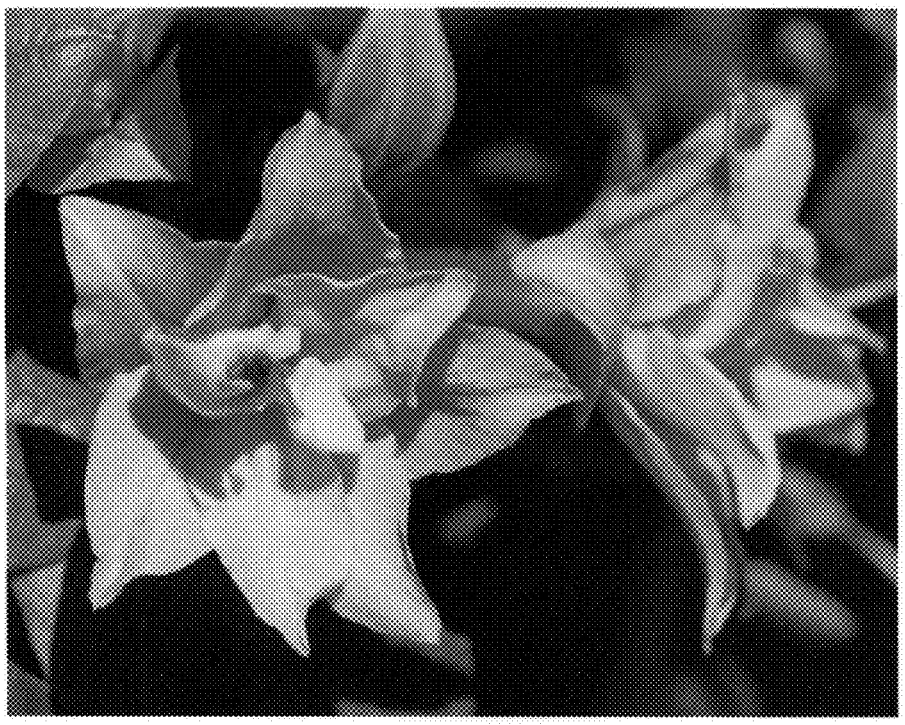

The photograph in FIG. 3 provides a close-up view of the flowers of 'UMNAZ 493'.

The colors in the photographs are as close as possible with the digital photography and printing techniques utilized and the color codes in the detailed botanical description accurately describe the new *Rhododendron.*

DETAILED BOTANICAL DESCRIPTION OF THE PLANT

The following is a detailed description of 24 year-old plants of the new cultivar as grown outdoors in an evaluation nursery in Excelsior, Minn. The plants were grown in day temperatures ranging from −21° to 39° C. and night temperatures ranging from −38° to 24° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

- *Blooming period*.—Up to 6 weeks beginning in late May to early June in Chanhassen, Minn.
- *Plant type*.—Deciduous shrub.
- *Plant habit*.—Upright, rounded, and densely branched.
- *Height and spread*.—Reaches 2.2 m in height and 1.9 m in spread.
- *Cold hardiness*.—At least to U.S.D.A. Zone 4a, flower buds are resistant to cold damage when exposed to temperatures down to −30° F.
- *Diseases*.—Observed to have foliage that is tolerant to powdery mildew.
- *Root description*.—Shallow and fibrous.
- *Propagation*.—Tissue culture (preferred) or softwood stem cuttings.
- *Growth rate*.—Slow to moderate.

Stem description:

- *Shape*.—Round.
- *Stem color*.—New growth; 144C to 144D, mature wood; 202A to 202C.
- *Stem size*.—Main stems; an average of 10.5 cm in length and 4 mm in width.
- *Stem surface*.—New growth; smooth and pubescent mature wood; smooth and glabrous.
- *Stem aspect*.—Held at an average angle of 15° (0°=vertical).
- *Branching*.—Densely branched.

Foliage description:

- *Leaf shape*.—Elliptic to obovate.
- *Leaf division*.—Simple.
- *Leaf base*.—Cuneate.
- *Leaf apex*.—Rounded.
- *Leaf venation*.—Pinnate, upper surface midrib 146C in color with lateral vein color matching leaf coloration, lower surface midrib and lateral veins 160B in color with short ciliate hairs on midrib NN155D in color.
- *Leaf margins*.—Entire and fringed with hairs 0.5 mm in length and NN155D in color.
- *Leaf attachment*.—Petiolate.
- *Leaf arrangement*.—Alternate.
- *Leaf internode length*.—An average of 1.5 cm and an average of 3 mm in foliage whirl at shoot apex.
- *Leaf orientation*.—Held horizontal to upright.
- *Leaf aspect*.—Cupped downward.
- *Leaf surface*.—Upper surface; smooth, glabrous, lower surface; smooth, glabrous with short hairs along midrib 0.5 mm in length.
- *Leaf color*.—Young leaves upper surface; 146B to 146C and young leaves lower surface; 191A, mature leaves upper surface; 137A to 137B transitioning to 147A in late summer and then ranging from 151A to 151D in the fall, mature leaves lower surface; 191A transitioning to 191C in late summer and into fall.
- *Leaf size*.—An average of 6 cm in length and 3 cm in width.
- *Leaf quantity*.—An average of 11 leaves per lateral branch 10.5 cm in length.
- *Petioles*.—Average of 5 mm in length and 1.5 mm in diameter, 145A in color, smooth, lightly pubescent surface.

Flower description:

- *Inflorescence type*.—Umbellate raceme.
- *Lastingness of flowers*.—An average of 21 days, self-cleaning.
- *Inflorescence size*.—Average of 8 to 12 cm in height and 10 to 15 cm in width.
- *Flower size*.—An average of 4.4 cm in depth and 5.5 cm in diameter.
- *Flower fragrance*.—Lightly fragrant.
- *Flower shape*.—Broad, tubular funnel.
- *Flower number*.—Average of 7 per lateral stem.
- *Flower aspect*.—Outward.
- *Flower bud*.—Obovate in shape, an average of 1.2 cm in length and 5.5 mm in diameter, acute apex, color; a blend of 144C and 145A with 58A near the apex in the summer and a blend of 165B, 166C, and 175C with overtones of 155C in the winter.
- *Flower attachment*.—Pedicellate.
- *Petal number*.—5 to 6 outer petals and 3 to 5 inner petals.
- *Petal shape*.—Outer petals; ovate to elliptic, inner petals; irregularly elliptic and slightly concave to rolled.
- *Petal color*.—Upper surface when opening; 55B, lower surface when opening 52B to 52C, upper surface when fully open 55D and marbled with 55B, upper surface of outer petal has blotch of 24A and 25A (occasional on upper surface of inner petal), lower surface when fully open 55B marbled with 51A and 55A, little color change prior to abscission but may develop 163A and 164B along the margins.

*Petal surface*.—Upper surface; glabrous and smooth to slightly rugose, lower surface; smooth, glabrous except for moderate pubescence along the midline.

*Petal margins*.—Outer petals; undulate and slightly rolled forward, inner petals; undulate.

*Petal apex*.—Outer petals; acute to acuminate, inner petals; obtuse to acuminate.

*Petal base*.—Fused.

*Petal size*.—Outer petals; an average of 2.5 cm in length and 1.7 cm in width, inner petals; 2.4 cm in length and 1.25 cm in width.

*Sepal number*.—5.

*Sepal shape*.—Oblong to lanceolate.

*Sepal margin*.—Entire and fringed with hairs 0.5 mm in length and N155A in color.

*Sepal size*.—Average of 3.5 mm in length and 2.5 mm in width.

*Sepal surface*.—Pubescent on upper and lower surface.

*Sepal apex*.—Obtuse to rounded.

*Sepal base*.—Fused.

*Sepal color*.—Immature upper surface; (not visible) enclosing base of the corolla tube, immature lower surface; 145A, mature upper surface; 144B and 58A near apex, mature lower surface a blend of 144A to 144B.

*Calyx*.—Shallow cup shape, an average of 4.5 mm in length and 6.5 mm in diameter.

*Pedicels*.—An average of 1 cm in length and 1.5 mm in diameter, smooth and lightly pubescent surface, 146C in color.

Reproductive organs:

*Gynoecium*.—1 Pistil, stigmas; elliptic to round in shape, 144A in color, 2 mm in diameter, style; 4 cm in length, curved and 51B to 51C in color, ovary; 146C in color.

*Androecium*.—Stamens; average of 5 when present (typically not present), fused or malformed in shape, anthers; oblong to elliptical in shape, 164C to 164D in color; pollen sparse in quantity and 155D in color.

*Fruit/seeds*.—Seed capsule; an average of 2 cm in length and 7.5 mm in width, exterior a blend of 165A and 166A in color, interior 167C to 167D in color, fruit; an average of 1.95 cm in length and 6.5 mm in diameter, 151A transitioning to 146D in color, seed; an average of 3 mm in length and 1.5 mm in width, 164A and 166C in color, 50 to 150 seeds per capsule.

It is claimed:

1. A new and distinct cultivar of *Rhododendron* plant named 'UMNAZ 493' as herein illustrated and described.

* * * * *